(12) United States Patent
Pearson (10) Patent No.: US 8,353,852 B2
(45) Date of Patent: Jan. 15, 2013

(54) OPHTHALMIC SIZING DEVICES

(75) Inventor: Andrew Robert Pearson, Charvil (GB)

(73) Assignee: LJT Projects Ltd., Maidenhead, Berkshire (GB)

( * ) Notice: Subject to any disclaimer, the term of this patent is extended or adjusted under 35 U.S.C. 154(b) by 161 days.

(21) Appl. No.: 12/864,387

(22) PCT Filed: Jan. 21, 2009

(86) PCT No.: PCT/GB2009/050045
§ 371 (c)(1), (2), (4) Date: Aug. 3, 2010

(87) PCT Pub. No.: WO2009/093067
PCT Pub. Date: Jul. 30, 2009

(65) Prior Publication Data
US 2010/0292616 A1    Nov. 18, 2010

(30) Foreign Application Priority Data

Jan. 24, 2008 (GB) .................................. 0801267.6
Dec. 12, 2008 (GB) .................................. 0822642.5

(51) Int. Cl.
*A61B 5/00* (2006.01)
(52) U.S. Cl. ...................................................... 600/587
(58) Field of Classification Search .............. 600/587; 604/8, 164.1, 289, 294, 295; 206/363–366, 206/438

See application file for complete search history.

(56) References Cited

U.S. PATENT DOCUMENTS 4,466,426 A * 8/1984 Blackman ..................... 604/187

(Continued)

FOREIGN PATENT DOCUMENTS

FR    2813522    9/2000

(Continued)

OTHER PUBLICATIONS

Cox, C W Jr.; "A technique for conjunctivo-dacryocystorhinostomy," American Journal of Opthalmology, vol. 72, No. 5, Nov. 1, 1971, pp. 931-933.
International Search Report for PCT/GB2009/050045 dated Jul. 22, 2009.
UK Search Report for GB0801267.6 dated Apr. 28, 2008.

*Primary Examiner* — Max Hindenburg
(74) *Attorney, Agent, or Firm* — Heslin Rothenberg Farley & Mesiti P.C.; Victor A. Cardona, Esq.

(57) ABSTRACT

An ophthalmic sizing device includes a sizing tube or set of such sizing tubes for use in determining a correct size of a bypass tube required in lacrimal surgery, each sizing tube having a flanged end at one end of a longitudinal length of tubing, the remaining end of the tubing distal to the flanged end having a series of ruled markings longitudinally along and towards the flange end. When used, a set of sizing tubes includes tubes having at least two relatively different absolute longitudinal lengths of tubing; and/or diameter flanges. The device can be in the form of a dilator having a sizing section. The use of such sizing devices allows the length of an ophthalmic bypass tube to be determined that leaves the tip of the bypass tube, when in situ, to protrude an optimally desired distance beyond the outer (lateral) nasal wall and into the nasal cavity of each particular patient, while remaining clear of the midline septum. Such a proud projection of bypass tubing helps prevent the bypass tube from being blocked after its permanent insertion.

15 Claims, 3 Drawing Sheets

U.S. PATENT DOCUMENTS

| | | | |
|---|---|---|---|
| 5,154,702 A * | 10/1992 | Foyil | 604/212 |
| 5,242,405 A * | 9/1993 | Howe | 604/125 |
| 5,593,393 A | 1/1997 | Trudell et al. | |
| 7,407,055 B2 * | 8/2008 | Rodriguez | 206/581 |
| 8,002,827 B2 * | 8/2011 | Deacon et al. | 623/5.12 |
| 2006/0276738 A1 * | 12/2006 | Becker | 604/8 |

FOREIGN PATENT DOCUMENTS

| | | |
|---|---|---|
| GB | 2442205 A | 4/2008 |
| WO | 2007094577 A1 | 8/2007 |

* cited by examiner

OPHTHALMIC SIZING DEVICES

CROSS REFERENCE TO RELATED APPLICATIONS

This application is a national stage filing under section 371 of International Application No. PCT/GB2009/050045, filed on Jan. 21, 2009, and published in English on Jul. 30, 2009 as WO 2009/093067 and claims priority of Great Britain Patent Application No. GB 0801267.6, filed on Jan. 24, 2008, and Great Britain Patent Application No. GB 0822642.5, filed on Dec. 12, 2008, the entire disclosures of which are incorporated herein by reference.

TECHNICAL FIELD

The present invention relates to medical devices that have their main application in corrective tear-duct surgery.

BACKGROUND ART

In healthy individuals, tear fluid (that is "lacrimal" fluid) is normally supplied continuously to their eyes from lacrimal glands, each being located in a lateral and superior relation to the respective eye. Upper lacrimal ducts feed the fluid from each gland to a respective conjunctival sac, in which the relevant eyeball is partially encased. The lacrimal fluid subsequently washes the sclera and other conjunctival components of the eye, as well as its cornea.

Figure 1A:
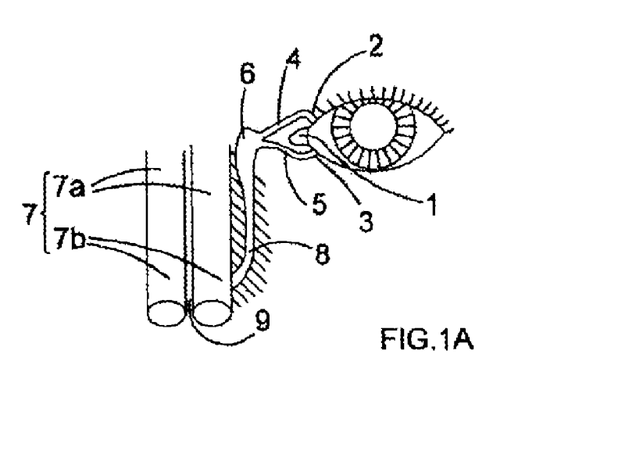

Under such healthy conditions, excess lacrimal fluid that cannot be retained by each eye and conjunctiva tends to be drained (see FIG. 1 of the drawings accompanying this specification) from the inner-canthus (1) (at the corner of the eye) to the nasal passages (7a,b), in particular to the inferior nasal meatus (7b). The nasal passages are separated by the nasal septum (9).

After any excess fluid has drained from the inner-canthus (1), it passes through a network of passages commencing with the puncta, which are seen as small papillae (2, 3) adjacent to the inner-canthus (1). From here, the lacrimal fluid is subsequently collected in the lacrimal sac (6), which is connected to the puncta via the canaliculi (4, 5). The lacrimal fluid is thereafter drained through the nasolacrimal duct (8) into the interior meatus (7b) of the nose.

Sometimes, if an unwanted closure of the passageways of the system occurs, for example by way of a blockage of any one or more of its sub-components, excess lacrimal fluid can no longer be disposed of in the usual way. Such a blockage can result from, inter alia, congenital anomalies, accidents, inflammation, advancing age, and so forth, and tends to cause the eye to continuously brim over with tears, with concomitant discomfort to the individual.

More seriously, if the blocked tears stagnate, they can become infected, which can then lead to inflammatory irritation of the mucous membranes of the affected passage. In turn this can result in proliferation of local epithelium, as well as hyperaemia, and even a purulent exudation into the conjunctiva. Infection caused in this way can ultimately lead to scarring over of the canaliculi (4, 5).

In severe cases, the resultant permanent closure can require a corrective surgical procedure. In some of these cases, only the defective portion of the lacrimal drainage system needs to be reconstructed. Thus, if the sole blockage occurs in, for example, the nasolacrimal duct the remaining lacrimal sac cavity can be joined directly with the mucosa of the nasal fossa, a procedure known as a dacryocystorhinostomy (DCR). This is typically achieved by removing tissue, including the intervening segment of nasal bone and periosteum, so that the drainage of tear liquid into the nose can be more or less restored.

In other cases, however, it may not be possible to re-connect or repair any part of the natural tear drainage system. Occasionally, the new connection after a DCR operation may be patent but fail to drain tears. In these situation the insertion of a replacement mechanical device (for example a bypass tube) is then required.

Conventionally, the bypass tube utilised in tear-duct surgery has been a small tube constructed of Pyrex™ glass, stiff plastic or some other relatively rigid material. However, usually it is Pyrex™-type glass that has been preferred, since this can neither be destroyed, nor corroded or otherwise affected by a patient's bodily fluids.

Figure 1B:
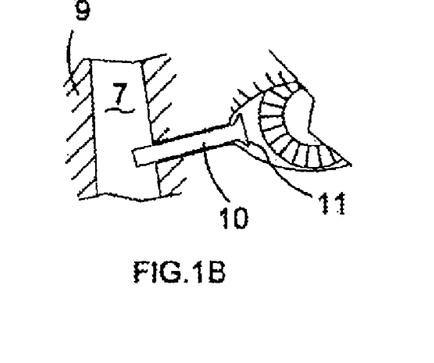

These tubes of Pyrex™ glass are generally known by surgeons as "Lester Jones" tubes, being named after their designer, Mr Lester T Jones, and are sometimes simply referred to as "Jones" tubes. Very similar devices go by the alternative trade names, such as "Callaghan Cox", "Gladstone Putterman", "Baylis", and "Naugle" tubes. As shown in FIG. 1B, these bypass tubes 10 have an external flange 11 that rests at the medial canthus and a length to accord with the patient's anatomy such that, after insertion into the inner corner of the eye, and then down the surgically created passage to the nose, they allow drainage of the excess lacrimal fluid internally into the nose.

Such operations to place bypass tubes have to date seldom been entirely successful, because at least the following two particular difficulties have typically been experienced.

Firstly, due to the lack of a firm attachment between the tube and the patient's tissues, as the tissues heal around the lower end portion of the inserted replacement tube, the latter is gradually rejected from the bone and flesh of the patient. And secondly, the internal opening of the tube may become obstructed either by the patient's flesh tending to heal over this opening if the tube is too short, or through impacting the midline nasal septum if it is too long.

Newer versions of improved Jones tubes have recently been developed, such as those constructed of frosted glass and those having collapsible flanges (see the present inventor's co-pending UK Patent Application no. 0619305.6) to try to overcome these difficulties. Even so, careful selection of the appropriate size of tube for the individual patient's anatomy is essential.

Each tube has a number of variables and each must be selected to be correct for the individual patient. For example, length of tube, external flange diameter and, where used, the location of the internal flange must all be selected.

Whereas the external flange diameter is usually either 3.5 mm or 4 mm, with the choice being at the surgeon's preference or guided by the visible external anatomy, in practice the area that presents a problem is the choice of the tube's length. What is ideally needed to be known is the length of tube that leaves the tip of the tube protruding the optimally desired distance beyond the outer (lateral) nasal wall and into the nasal cavity, whilst remaining clear of the midline septum. Such a proud projection of tubing helps prevent the tube from being blocked after its permanent insertion.

Figure 2:
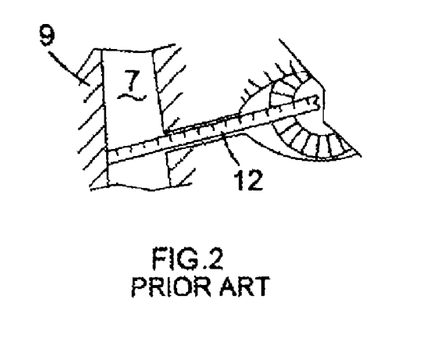
FIG. 2 illustrates conventional use of the dipstick method for determining the dimensions of a patient's anatomy.

At present this selection is made by educated guesswork (most patients require a tube from only a limited range of lengths) or by using a dipstick 12 (see FIG. 2) passed down the track being formed to take the tube. The dipstick 12 touches the midline nasal septum 9, so being prevented from further insertion. The distance from midline septum to where the head of the bypass tube is expected to lie is then read off the externally visible portion of the dipstick. A sleeve slid down the dipstick which rests on the medial canthus may be used to assist the estimation of this distance. An estimated length of around between 1-3 mm is deducted by the surgeon from this maximum length of dipstick insertion to provide a figure for the size of bypass tube required so as not to impact the midline nasal septum.

When the decision of required length is approached using the dipstick method, at least four main limitations are evident.

Figure 3A:
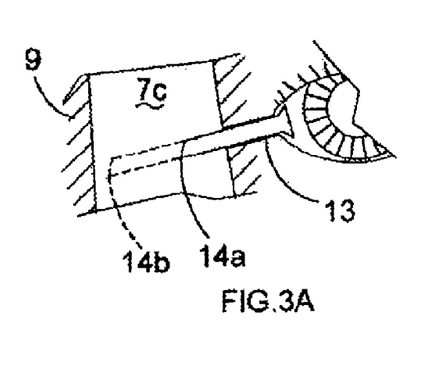
Figure 3B:
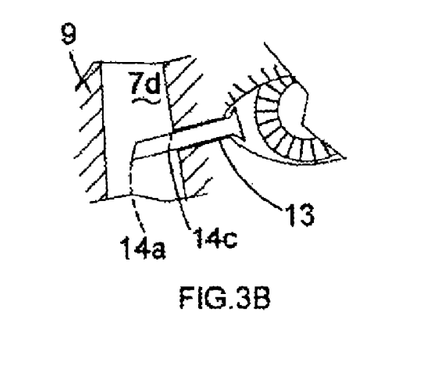

Firstly, the dipstick method determines the distance of the tip of the tube from the midline septum but, given that the space inside the nose is very different between individual patients, this provides no real accuracy regarding how far it is beyond the lateral wall. Indeed, as shown in FIGS. 3a and b, in a very tight nasal space 7d the tube might barely 14c enter the nose using this method, whilst in a very wide nasal space 7c the length 14b of tube protruding into the nose may be much greater than needed (14a).

Secondly, due to the flexibility and elasticity of the tissues in the medial canthal region where the external flange of the bypass tube will rest, the estimation of the total distance from the nasal septum to this point is inherently inaccurate. An incorrect length of bypass tube may therefore be selected.

Thirdly, a dipstick is merely a metal stick with a scale on its length that is held in the track created. The track angle and/or direction may not be exactly the one that the tube will eventually lie on once it has been placed in situ, thus the length calculated by the dipstick method has another degree of inaccuracy.

Fourthly, the tip of the dipstick must contact the nasal septum and in doing so is liable to cause some trauma to the mucosa surface.

When considering the question of whether it matters that the length is difficult to calculate accurately using this technique, one might wonder why surgeons do not simply try out different lengths until the right one is found. In practice, before the present invention, this is precisely the method to which most surgeons had to resort. They selected the best guess length possible, tried it in situ, looked inside the nose with an endoscope and either left it if it was correct or replaced it with a longer or shorter one according to how it looked inside the nose.

For most patients, two or three or even more bypass tubes might be used before the correct size is found. The tubes that have been placed in situ during this method that have been found to be of the incorrect size and thus removed could not be re-used in other patients even if cleaned and re-sterilised. Hence, the actual total cost for bypass tubes used is usually higher than for the individual tube that is left in the patient at the end of the operation. Whilst this in itself may not be a very significant extra expense when using relatively cheap standard tubes, the increasing use of newer frosted or collapsibly flanged tubes is made more expensive.

Thus, it is becoming more and more cost-effective to ensure that the tube length selection is right first time.

One aim of the present invention is to provide a very accurate and simple system for ensuring that the initial selection of length for the bypass tube is correct.

DISCLOSURE OF INVENTION

Thus, according to one aspect, the present invention provides an ophthalmic sizing device as claimed in accompanying claim 1.

According to a second aspect, the present invention provides a set of ophthalmic sizing tubes as claimed in claim 5 or 7.

According to a third aspect, the present invention provides, as claimed in claim 21, a combination set of a sizing device or a set of ophthalmic sizing tubes as mentioned above with one or more bypass tubes.

According to a fourth aspect, the present invention provides, as claimed in claim 24, a combination set of a sizing device or a set of ophthalmic sizing tubes as mentioned above together with introducer equipment.

According to a fifth aspect, the present invention provides a method as claimed in claim 25 for selecting a bypass tube of correct size.

Further advantageous and optional features are mentioned in the accompanying subsidiary claims.

The individual and sets of sizing devices are typically manufactured of a cheap material, each device having the same general shape as that of the eventually used bypass tube, albeit that sizing devices of the same or of differing length may be part of the same set.

The sizing devices need not themselves be tubes having a lumen, but can also alternatively be solid, that is without a lumen. A dilator device may be used to make the track into the nose and along which first such sizing tubes and then the permanent bypass tube will pass.

The sizing devices may also be part of adapted dilators themselves, either having a lumen or not, each again being the dilator used to make the track into the nose along which eventually the permanent bypass tube will pass, and being adapted by their sizing part having a series of sizing markings upon the surface of its leading length.

In use, a sizing device is chosen of approximately the correct length for the particular patient and then placed in situ like the final replacement tube. The positioned sizing device is left to settle for a moment to adopt its natural position and then it is viewed internally through the nose with an endoscope.

From the part of the internal scale on the sizing device that is visible using the endoscope, the desired position of the internal most tip of the bypass tube, and internal flexible flange if used, can be noted, which in turn is used to determine the correct length of bypass tube, as well as correct flange position, required for that patient. The sizing device can then be removed and the appropriate permanent bypass tube inserted.

The present invention will now be described, in a non-limiting way, by the following preferred examples with reference to, and as illustrated in, the accompanying figures, in which:

BRIEF DESCRIPTION OF DRAWINGS

FIG. IA schematically illustrates the functional anatomy of a normal and healthy tear-duct system;

FIG. IB schematically shows a conventional bypass tube in situ after lacrimal surgery;

FIGS. 3 A and B show how potential inaccuracies can occur using the dipstick approach as illustrated in FIG. 2;

FIG. 4 A shows a side view of two sizing tubes that are part of a set according to one embodiment of the present invention;

FIG. 4 B shows an end view of the two sizing tubes depicted in FIG. 4A;

FIG. 5 A shows an end view of one of the sizing tubes illustrated in FIG. 4B;

BEST MODE FOR CARRYING OUT THE INVENTION

Figure 4A:
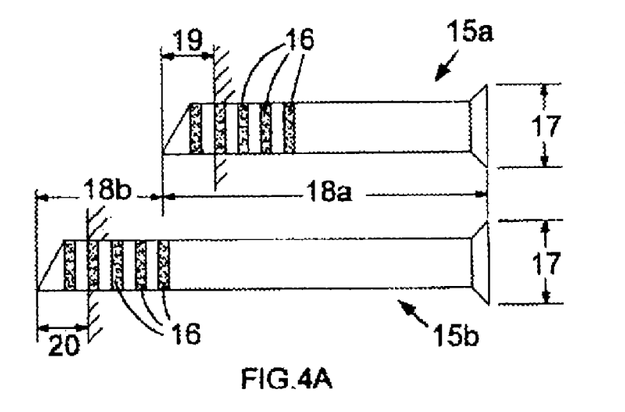
Figure 4B:
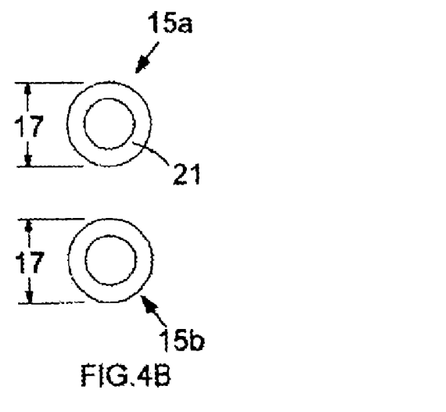

A set of two sizing devices 15a, b is shown in FIG. 4A. Each of these illustrated sizing devices is a tube having a lumen, although alternatively each device could be a solid cylindrical device (not shown), that is, being a device not having a lumen.

The tube illustrated in FIG. 4A has an easily visible series of marked bands 16 at an end furthest away from the flanged end that prevents it from passing too far down the surgically formed passage and secures it at the inner canthus 1 of the eye when it is in situ.

The marked bands are useful for determining not just the overall length of the bypass tube to be used in a permanent capacity, but also for determining the flange position for those bypass tubes that incorporate such an internal flange.

Often the base of these internal flanges is spread over, for example approximately 1.5 mm, its site on the respective bypass tube. To provide a clearer visual impression of where the flange will be relative to the lateral nasal wall it can therefore be useful, for example, to make a small number of segments (for example four) of each of the rings of an equivalent width (i.e. 1.5 mm thickness), which will be much broader than the rest of the marking around the sizing tube. In this way, the total length of the required bypass tube can be determined as well as the position (i.e. distance from the external flange) of its internal flange if the latter is used.

This level of precision is especially useful when bypass tubes are being 'tailor-made' for each patient's nose with the internal flange being at a variable distance from the internal tip.

The series of bands 16 serves to form a scale or ruler that can be easily seen when viewed with an endoscope placed internally within the nose. Typically, the sizing tubes are manufactured of a rigid white plastic with black marked bands for ease of visibility, although any alternative arrangement that forms a vividly contrasting series of markings can be used.

Likewise, any arrangement (see FIGS. 6 A to F) providing a series of markings that can clearly be distinguished, for example elevations (23, 25), depressions (24, 26) and so forth, can be used on the sizing tube to provide the scale/ruler. Thus, instead of alternating black and white bands, a series of alternating elevated and non-elevated (or depressed and non-depressed, and so forth) sections of the outer wall of the tube can provide the series of markings required.

Figure 6A:
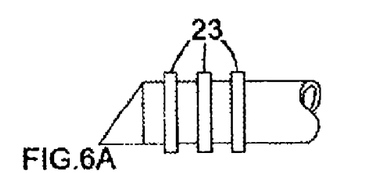
FIGS. 6A to F each show a side view of alternative types of markings that can be present on sizing tubes according to various embodiments of the present invention.
Figure 6B:
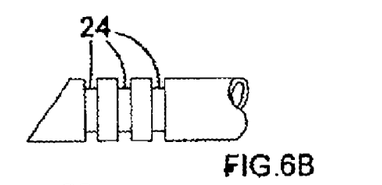
Figure 6C:
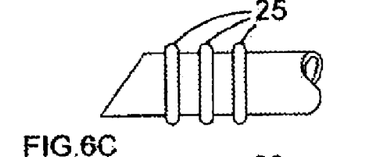
Figure 6D:
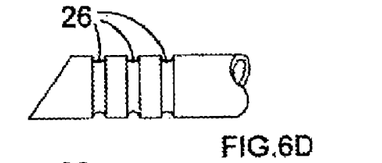
Figure 6E:
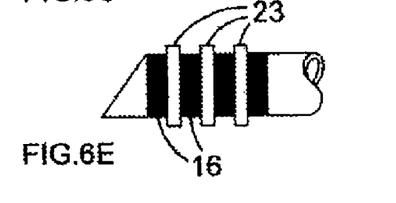
Figure 6F:
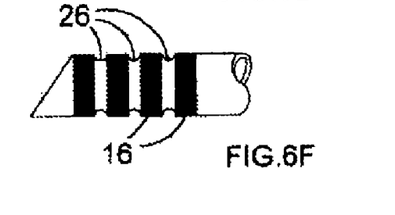

Such elevations and depressions may be rounded (25, 26) or square-ended (23, 24), or any shape as desired, so long as they present a clear marking when viewed. Indeed, markings in the form of coloured bands (16) as described above can be interleaved (see FIGS. 6E and F) with markings involving elevations or depressions, and so forth.

Further, the markings need to be large enough as well as contrasting enough so that it is easy to determine the size of replacement bypass tube, as well as internal flange position if used, required when the markings are viewed.

Generally, the sizing devices are of a relative size themselves that permits determination of the likely range of sizes of bypass tubes required for a range of different patients. For example, in FIG. 4A are shown two sizing tubes (15a, b) of differing length each available with different (typically 3.5 and 4.0 mm) diameter external flanges.

Alternatively, a single sizing device can be used instead of a set. The sizing device is similarly inserted in situ, its markings viewed and it is then withdrawn and replaced with the appropriate length of permanent bypass tube. If the single sizing device is too long and so impacts the nasal septum, by manufacturing it of a relatively soft material that can be easily cut by the surgeon or surgical assistant, it can be trimmed to the correct length for insertion before its markings are viewed inside the nasal meatus.

Figure 5A:
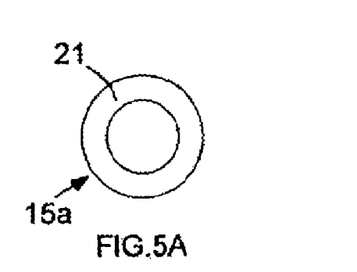
Figure 5B:
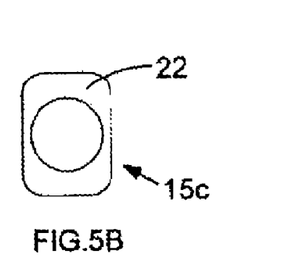
FIG. 5B shows an end view of a sizing tube having a substantially rectangular flange according to one embodiment of the present invention.

In addition, it is also possible (see for example 15a and 15c in FIGS. 5 A and B) for the sizing device(s) (whether used as a single device capable of being trimmed or as a set of devices of differing lengths) to have relatively differing external flange designs (21, 22) that, for example, match with the correspondingly different designs of external flanges present on the various non-Jones types of bypass tube.

Thus, for example, the external flange of a Naugle bypass tube has a cross-sectional profile that is approximately rectangular (thus see 22 of 15c) as opposed to the round shape of the Jones tube, with the tips of its corners slightly rounded off. The Naugle external flange has in effect substantially the same 'diameter' for its longest cross-sectional dimension as that of a Jones tube flange, the advantage being that a neater fit into the medial canthal region is provided and therefore greater stability.

Each of the different sized lengths of sizing devices will allow measurement over several millimeters.

Preferably, each sizing device is relatively inexpensive to manufacture and so not liable to being redundant by use of the replacement Jones bypass tubes themselves.

Figure 7A:
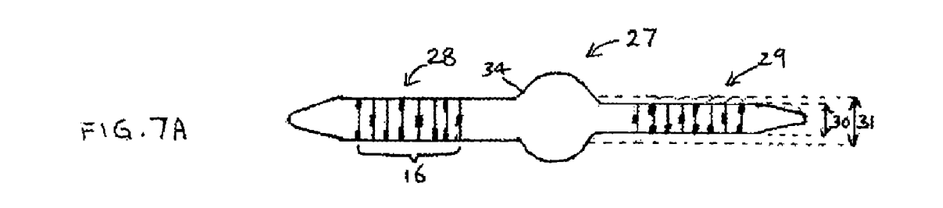
FIGS. 7A to D illustrate dilators, being adapted to have sizing parts, which can be used as the sizing devices of the present invention according to alternative embodiments.

The sizing devices may alternatively be adapted dilators, as shown in FIGS. 7A to D, each dilator 27 having a sizing part that comprises a ruler section 16. Thus, such a dilator typically comprises one or more dilating elements 28, 29, each element attached at a shoulder 34 to a section having a larger diameter than that of the element. Further, typically each element has a different diameter, thus for example as shown in FIG. 7A a first element 28 has a larger diameter 31 than that 30 of a second element 29.

Figures 7B, 7C:
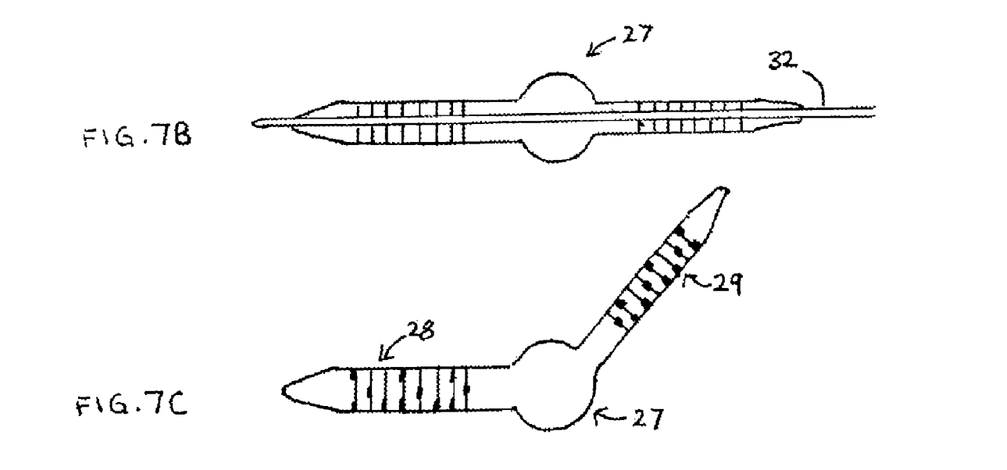
Figure 7D:
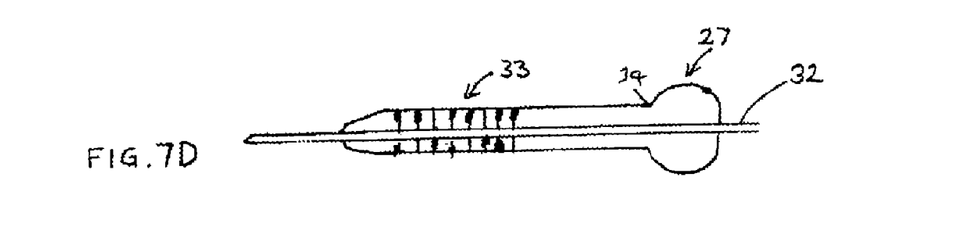

The dilator shown in FIG. 7A may have a lumen through which a guiding wire 32 passes, as illustrated in FIG. 7B, along which the dilator may be guided when making the track along which the permanent bypass tube will eventually pass when inserted.

Alternatively, as shown in FIG. 7C, the elements 28, 29 may be arranged in a nonlinear manner to form an angle about the central section.

In a further embodiment (see FIG. 7D) the dilator 27 used as a sizing device may comprise a sole element 33 having the sizing part.

Preferably, the sizing devices are packaged pre-sterilised for ease of use.

In use, each length of sizing device will be determined so that when it is in situ its internalised end sits proud of the nasal mucosa, hence allowing some length of marked tubing to be visible by endoscopy within the nasal meatus. Thus, in relation to sizing tube 15a, a length 19 of tubing (being the most internal part of its length 18a) is proud of the nasal mucosa, whereas for larger (that is of length 18a plus 18b) sizing tube 15b (used for a relatively larger patient), the length 20 is proud.

In summary, the present invention provides a simple and relatively less expensive solution to the problem of accurately and quickly determining the correct length of bypass tube to use during corrective lacrimal surgery.

The invention claimed is:

1. An ophthalmic sizing be for use in determining a correct size of a bypass tube required in tear-duct surgery, said ophthalmic sizing tube consisting of a cylindrical tubular element having a longitudinal length, the tabular element defining a lumen, and the tubular element defining a flanged end at one end of the tubular element, the remaining length of the tubular element distal to the flanged end having a series of ruled markings, the series extending longitudinally along the remaining length and towards the flanged end, and the markings being visible by virtue of at least one of:
    a contrast between color of the markings and color of the remainder of the element over which the markings are located, and
    the markings being raised or depressed with respect to intervening sections of the tubular element;
    such that in use the ophthalmic sizing tube may be inserted into a drainage passage made during tear-duct surgery, the drainage passage extending from an eye to a nasal passage, with the flanged end locating at the inner canthus of the eye, the markings within the nasal passage being visible.

2. A set of ophthalmic sizing tubes for use in determining a correct size of a bypass tube required in tear-duct surgery comprising: a plurality of sizing tubes as claimed in claim 1, wherein the plurality of sizing tubes comprises sizing tubes of at least two relatively different absolute longitudinal lengths.

3. A set of sizing tubes as claimed in claim 2, wherein the plurality of sizing tubes comprises sizing tubes having at least two relatively different diameters of flanges at their flanged ends.

4. A set of ophthalmic sizing tubes for use in determining a correct size of a bypass tube required in tear-duct surgery comprising: a plurality of sizing tubes as claimed in claim 1, wherein the plurality of sizing tubes comprises sizing tubes having at least two relatively different diameters of flanges at their flanged ends.

5. A sizing tube as claimed in claim 1, manufactured of a material that may be cut and trimmed to a desired length.

6. A sizing tube as claimed in claim 1, manufactured of a plastic or silicone material.

7. An ophthalmic dilator for use in determining a correct size of a bypass tube required in tear-duct surgery, said ophthalmic dilator defining a lumen and defining a cylindrical tubular element having a longitudinal length, and a shoulder to a portion having a larger diameter at one end of the cylindrical tubular element, the end of the tubular element distal to the shouldered end having a series of ruled markings, the series extending longitudinally along the tubular element and towards the shouldered end, and the markings being visible by virtue of at least one of:
    a contrast between color of the markings and color of the remainder of the element over which the markings are located, and
    the markings being raised or depressed with respect to intervening sections of the tubular element;
    such that in use the ophthalmic dilator may be guided along a drainage passage made during tear-duct surgery, the drainage passage extending from an eye to a nasal passage, until the shouldered end locates at the inner canthus of the eye, the markings within the nasal passage being visible.

8. An ophthalmic dilator for use in determining a correct size of a bypass tube required in tear-duct surgery, said ophthalmic dilator defining a lumen and defining a plurality of cylindrical tubular elements each having a longitudinal length, and a shoulder to a portion having a larger diameter at one end of the cylindrical tubular element, the tubular elements being joined together at the portions of larger diameter, the end of each tubular element distal to the shouldered end having a series of ruled markings, the series extending longitudinally along it and towards the shouldered end, and the markings being visible by virtue of at least one of:
    a contrast between color of the markings and color of the remainder of the element over which the markings are located, and
    the markings being raised or depressed with respect to intervening sections of the tubular element;
    such that in use one of the cylindrical tubular elements may be guided along a drainage passage made during tear-duct surgery, the drainage passage extending from an eye to a nasal passage, until the shouldered end locates at the inner canthus of the eye, the markings within the nasal passage being visible.

9. A sizing tube as claimed in claim 1, wherein one or more segments of each marking has a greater width, in a direction parallel to that of the longitudinal axis of its element, than the width of the remaining segments of the same marking.

10. A sizing tube as claimed in claim 1, wherein the tubular element is sterile.

11. A combination set of a sizing tube as claimed in claim 1 and further comprising one or more bypass tubes for use in lacrimal corrective surgery.

12. A combination set as claimed in claim 11, further comprising introducer equipment for finding a drainage passage for each tube to lie on, the drainage passage extending from the eye to the nasal passage, and for dilating the passage to a desired diameter.

13. A combination set of a sizing tube as claimed in claim 1 further comprising introducer equipment for performing at least one of:
    finding a passage extending from the eye to the nasal passage for each tube to lie on; and
    dilating the passage to a desired diameter.

14. A method of using a set of sizing tubes as claimed in claim 2, comprising the steps of: choosing a sizing tube of approximately correct length, placing the chosen sizing tube in situ in a surgically formed passage in a patient so that part of its distal length lies proud of the patient's nasal mucosa, and reading the position of the markings on the distal length lying proud so as to determine a correct length, in the particular patient, of a permanent bypass tube to be used as a replacement for the chosen sizing tube.

15. A method of using a sizing tube as claimed in claim 1, comprising the steps of:
    placing the sizing tube in situ in the surgically formed drainage passage in a patient, the path extending from an eye to a nasal passage of the patient, so that the flanged end locates at the inner canthus of the eye and that part of its distal length lies proud of the patient's nasal mucosa;
    reading the position of the markings on the distal length lying proud of the patient's nasal mucosa within the nasal passage; and so
    determining a correct length, in the particular patient, of a permanent bypass tube to be used as a replacement for the sizing tube.

* * * * *

UNITED STATES PATENT AND TRADEMARK OFFICE
CERTIFICATE OF CORRECTION

PATENT NO. : 8,353,852 B2  
APPLICATION NO. : 12/864387  
DATED : January 15, 2013  
INVENTOR(S) : Andrew Robert Pearson Page 1 of 1

It is certified that error appears in the above-identified patent and that said Letters Patent is hereby corrected as shown below:

Column 7, Line 5: Claim 1, Delete "be" and insert --tube--

Signed and Sealed this  
Twelfth Day of March, 2013

Teresa Stanek Rea  
*Acting Director of the United States Patent and Trademark Office*

UNITED STATES PATENT AND TRADEMARK OFFICE
CERTIFICATE OF CORRECTION

PATENT NO. : 8,353,852 B2  
APPLICATION NO. : 12/864387  
DATED : January 15, 2013  
INVENTOR(S) : Andrew Robert Pearson It is certified that error appears in the above-identified patent and that said Letters Patent is hereby corrected as shown below:

In the Claims:

Column 7, Line 8: Claim 1 Delete "tabular" and insert --tube--

This certificate supersedes the Certificate of Correction issued March 12, 2013.

Signed and Sealed this  
Twenty-first Day of May, 2013

Teresa Stanek Rea  
*Acting Director of the United States Patent and Trademark Office*

UNITED STATES PATENT AND TRADEMARK OFFICE
CERTIFICATE OF CORRECTION

PATENT NO.         : 8,353,852 B2                                  Page 1 of 1
APPLICATION NO.    : 12/864387
DATED              : January 15, 2013
INVENTOR(S)        : Andrew Robert Pearson It is certified that error appears in the above-identified patent and that said Letters Patent is hereby corrected as shown below:

In the Claims:

Column 7, Line 5, Claim 1, Delete "be" and insert -- tube --.

Column 7, Line 8, Claim 1, Delete "tabular" and insert -- tubular --.

This certificate supersedes the Certificates of Correction issued March 12, 2013 and May 21, 2013.

Signed and Sealed this
Twentieth Day of August, 2013

Teresa Stanek Rea
*Acting Director of the United States Patent and Trademark Office*